United States Patent [19]

Iwataki et al.

[11] Patent Number: 4,579,971
[45] Date of Patent: Apr. 1, 1986

[54] CYCLOHEXANE DERIVATIVES

[75] Inventors: Isao Iwataki, Minamiashigara; Kagari Fujita, Hadano; Hisao Ishikawa, Odawara; Hideo Hosaka, Hiratsuka; Kenichi Kohara, Ohisomachi, all of Japan

[73] Assignee: Nippon Soda Co. Ltd., Tokyo, Japan

[21] Appl. No.: 715,922

[22] Filed: Mar. 25, 1985

Related U.S. Application Data

[63] Continuation-in-part of Ser. No. 461,000, Jan. 26, 1983, Pat. No. 4,515,729.

[51] Int. Cl.$^4$ ............................................. C07C 83/00
[52] U.S. Cl. ............................................. 564/300; 71/98
[58] Field of Search .................. 564/300; 71/97, 98, 71/103, 121

[56] References Cited

U.S. PATENT DOCUMENTS 3,950,420 4/1975 Sawaki et al. ................. 564/300
4,249,937 2/1981 Iwataki et al. ................. 564/300 X Primary Examiner—Robert V. Hines
Attorney, Agent, or Firm—George B. Oujevolk

[57] ABSTRACT

A cyclohexane derivative having the formula

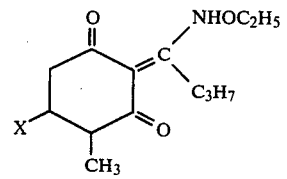

wherein X is 2-(ethylthio)propyl or 2-(4-chlorophenylthio)ethyl.

1 Claim, No Drawings

CYCLOHEXANE DERIVATIVES

This application is a continuation-in-part of U.S. patent application Ser. No. 461,000 filed on Jan. 26, 1983 and now U.S. Pat. No. 4,515,729.

The present invention relates to substituted cyclohexane-1,3-dione derivatives, to a process for the preparation thereof, and their uses as selective herbicides.

According to the present invention, there is provided a cyclohexane derivative having the formula:

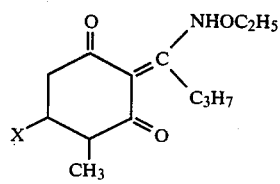
(I)

wherein X is 2-(ethylthio)propyl or 2-(4-chlorophenylthio)ethyl.

The cyclohexane derivatives of the formula (I) have superior herbicidal activity and are particularly effective in the control of grass weeds, such as barnyardgrass (*Echinochloa crus-galli*), blackgrass (*Alopecurus myosuroides*), crabgrass (*Digitaria sanguinalis*), wild oat (*Avena fatua*) and Johnsongrass (*Sorghum halepense*), and they hardly injure broad leaf crops such as beans, peas, radish, beets and cucumber.

A part of the present inventors originally invented and discovered that some 5-alkylthio(sulfinyl or sulfonyl)alkyl cyclohexane-1,3-dione derivatives have herbicidal activities, as disclosed in, for example, U.S. Pat. No. 4,249,937. The inventors have found that cyclohexane-1,3-dione derivatives of formula (I), which possess methyl group at the 4-position, are not only as herbicidally active as the pervious invention but also they exhibit more improved effectiveness in the killing crabgrass and barnyardgrass than the foregoing cyclohexane-1,3-dione derivatives. That is, the present compounds kill crabgrass and barnyardgrass almost perfectly at 12.5 g/10a, while said known compounds, for example, the comparative compounds 1 and 2 showed only a degree of damage of 40 to 79% (4, 5, 6 and 7 as scale of value to such two weeds at the same application rate in post-emergence treatment.

Furthermore, between those two kinds of the compound groups, there is a significant difference in the herbicidal activity in pre-emergence treatment. That is, said known compounds were quite insufficient to control such two weeds even at 200 g/10a and needed more dosage to obtain the satisfactory effect, while the present compounds killed the weeds almost perfectly at 100 g/10a.

Therefore, the present compounds can kill such weeds sufficiently at the dose less than one-half of said known compounds.

Thus, it is clear that the present compounds are significantly improved in herbicidal activity compared with the known compounds having similar structure formulae which do not have methyl radical on 6 position of their cyclohexane-dione ring.

The present compounds can be prepared in accordance with the following equation:

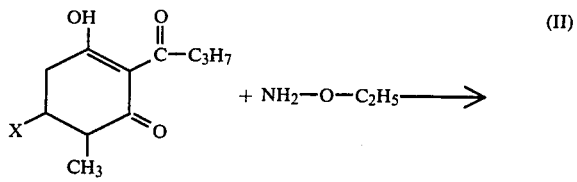

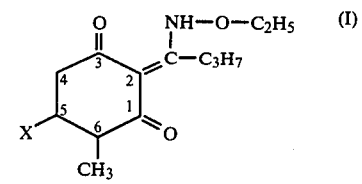

wherein X is as previously defined.

The above reaction can be conducted in an inert solvent.

As an inert solvent, acetone, diethyl ether, methyl alcohol, ethyl alcohol, isopropyl alcohol, benzene, tetrahydrofuran, chloroform, acetonitrile, dichloroethane, dichloromethane, ethyl acetate, dioxane, toluene, xylene, dimethyl sulfoxide or the like may be used.

The reaction temperature may be from $-10°$ C. to the boiling point of the reaction solution, preferably from $10°$ to $60°$ C., and the reaction may be carried out for several hours or longer.

After the reaction has been completed, the solvent is, if necessary, removed and the reaction mixture is then extracted with an alkaline solution, or is poured into ice-cold water. The alkaline extract or the mixture with water is acidified with hydrochloric acid, and the crude product is isolated from the acidified mixture by extraction with solvent or by filtration.

If the product is crystalline, the crude product can be purified by recrystallization, and if the product is an oily substance, the crude product can be purified by distillation or isolation by column chromatography.

A chemical formula of the resulting purified compound can be assigned based on the results of an elemental analysis, NMR spectrum and IR spectrum.

It is expected that the compounds represented by the formula (I) exist in the following four tautomeric forms:

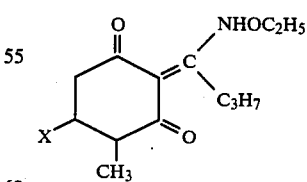

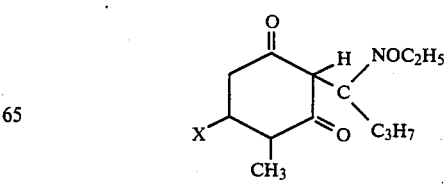

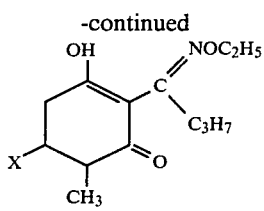

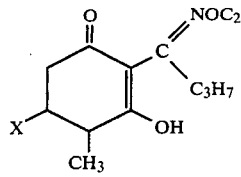

It is further expected that the compounds represented by the formula (II) exist in the following three tautomeric forms:

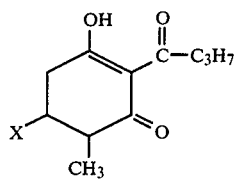

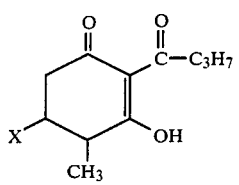

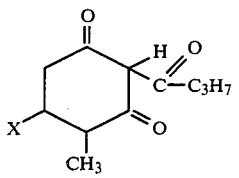

The starting material of the formula (II) can be prepared in accordance with the following equation wherein R is preferably lower alkyl:

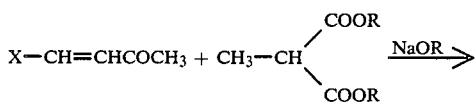

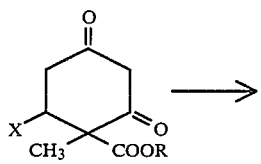

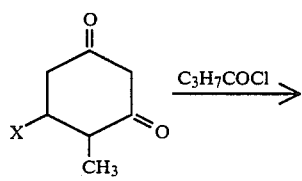

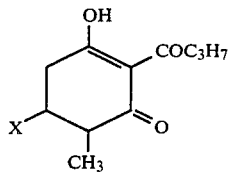

The following Examples illustrate the invention.

EXAMPLE 1

2-(1-ethoxyaminobutylidene)-5-(2-ethylthiopropyl)-4-methylcyclohexane-1,3-dione (Compound No. 1)

Into 10 ml of ethanol, 2.97 g of 2-butyryl-5-(2-ethylthiopropyl)-4-methylcyclohexane-1,3-dione was dissolved and 0.81 g of ethoxyamine was dropped thereto at 0° C. and the resulting solution was stirred at room temperature for 3 hours. After pouring the reaction solution into ice-cold water, the mixture was extracted with chloroform. The chloroform solution was washed with water and extracted with 1N-sodium hydroxide solution. The sodium hydroxide solution was acidified with 1N-hydrochloric acid and the acidified mixture was extracted with chloroform. The chloroform solution was washed with water and dried over anhydrous magnesium sulfate. The removal of chloroform from said chloroform solution by distillation under reduced pressure gave 3.0 g of the desired product as yellow oily material.

Yield 88%, $n_D^{19.5}$ 1.5375.

Inclusive of the above, the compounds embodying this invention which can be prepared in an analogeous manner are tabulated in Table 1.

TABLE 1

| Compound No. | X | Physical Constant |
|---|---|---|
| 1 | C$_2$H$_5$SCHCH$_2$— <br> \| <br> CH$_3$ | $n_D^{19.5}$ 1.5375 |
| 2 | Cl—⟨⟩—SCH$_2$CH$_2$— | $n_D^{25}$ 1.5711 |

As mentioned previously, the compounds possess superior herbicidal activity. The compounds may be applied directly to the soil as pre-emergence treatment or as post-emergence treatment to plant foliage, or they can be mixed intimately with soil. The compounds may be applied to soil or to plant foliage in amounts of 5 g or more per 10 are.

A herbicidal composition containing the compound as its active ingredient may be formulated by mixing it with suitable carriers in a form generally used in agricultural chemicals, such as wettable powder, emulsifiable concentrate, granular formulation, water soluble powder and aerosol. As solid carriers, bentonite, diatomaceous earth, apatite, gypsum, talc, pyrophyllite, vermiculite and clay may be used. As liquid carriers, kerosene, mineral oil, petroleum, solvent naphtha, benzene, xylene, cyclohexane, cyclohexanone, dimethylformamide, alcohol and acetone may be used. A surface active agent may also be added, in order to give a homogeneous and stable formulation.

The compounds can be used as an admixture with other agriculturally effective chemicals, so long as those are safely and stably compatible with the compounds. Such chemicals can be, but are not restricted to, the classes of chemicals commonly known as plant nutrients, fertilizers, insecticides, acaricides, fungicides, herbicides and nematocides.

For admixture of the compound with known herbicides, the use is recommended of triazine derivatives such as simazine, propazine and prometryn, carbamate derivatives such as phenmedipham, urea derivatives such as metabenzthiazuron and linuron, and heterocyclic compounds such as pyrazon and lenacil.

The concentration of the active ingredient in a herbicidal composition may vary according to type of formulation, and the concentration is, for example, in the range of 5–30 weight percent, preferably 10–20 weight percent, in wettable powder; 5–70 weight percent, preferably 20–60 weight percent, in emulsifiable concentrates; and 0.5–30 weight percent, preferably 1–10 weight percent, in granular formulation.

A wettable powder or an emulsifiable concentrate thus produced may be diluted with water to a specified concentration and used as a liquid suspension or a liquid emulsion for treating soils or plant foliage. Further, a granular formulation may be directly used for soil or foliage treatment.

Non-limiting examples of herbicidal compositions are illustrated as follows.

EXAMPLE 2

Wettable Powder

Compound No. 1 10 parts by weight
White carbon 25 parts by weight
Diatomaceous earth 57 parts by weight
Sodium alkylsulfate 8 parts by weight These were mixed homogeneously and reduced to fine particles to provide a wettable powder containing 10% of active ingredient. At use, it is diluted to a desired concentration with water, and is sprayed as a suspension.

EXAMPLE 3

Emulsifiable Concentrate

Compound No. 2 40 parts by weight
Xylene 35 parts by weight
Dimethylformamide 15 parts by weight
Polyoxyethylene phenylether 10 parts by weight These were mixed together to provide an emulsifiable concentrate containing 40% of the active ingredient. At use, it is diluted to a desired concentration with water, and is sprayed as an emulsion.

EXAMPLE 4

Granular Formulation

Compound No. 1 7 parts by weight
Talc 38 parts by weight
Clay 38 parts by weight
Bentonite 10 parts by weight
Sodium alkylsulfate 7 parts by weight These were mixed homogeneously and reduced to fine particles. The fine particles are made into granules, each having a diameter in the range of 0.5–1.0 mm, to provide a granular formulation containing 7% of the active ingredient. At use, it is directly applied.

The herbicidal effects of compounds are illustrated by the following tests.

TEST 1

Post-emergence treatment

Seeds of crabgrass and barnyardgrass were planted in each pot having a surface area of 100 cm$^2$. When the plants were grown to tillering stage and 3–5 leaf stage respectively, an aqueous emulsion, prepared by diluting an emulsifiable concentrate with water to a specified concentration (125, 62.5 ppm), was sprayed on the foliage of the test plants at a rate of 100 1/10 are, and the pots were kept in a greenhouse. Three weeks after spraying, the degree of damage to the each plant was observed and evaluated on the scale of values of 0–10, which has the following meanings:

| Scale of Value | Degree of Damage |
| --- | --- |
| 0 | 0% |
| 2 | 20–29% |
| 4 | 40–49% |
| 6 | 60–69% |
| 8 | 80–89% |
| 10 | 100% |

1, 3, 5, 7 and 9 mean the intermediate degree between 0 and 2, 2 and 4, 4 and 6, 6 and 8, and 8 and 10 respectively.

The results are shown in Table 2.

TABLE 2

| Compound No. | Application Rate of Active Ingredient (g/10a) | Degree of Damage | |
| --- | --- | --- | --- |
| | | Crabgrass (tillering stage) | Barnyard grass (3–5 leaf stage) |
| 1 | 12.5 | 10 | 10 |
| | 6.25 | 7 | 8 |
| 2 | 12.5 | 9 | 9 |
| | 6.25 | 8 | 7 |
| Comparative Compound 1 | 12.5 | 6 | 7 |
| | 6.25 | 4 | 5 |
| Comparative Compound 2 | 12.5 | 7 | 4 |
| | 6.25 | 5 | 1 |

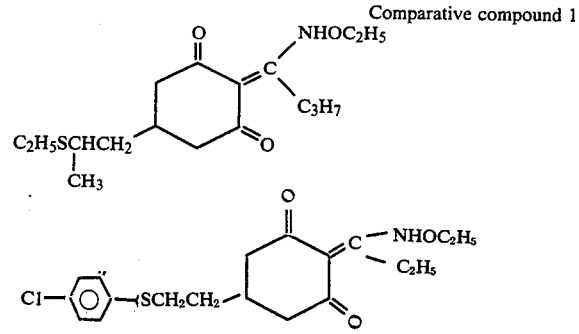

Comparative compound 1

Comparative compound 2

Test 2

Pre-emergence Treatment

Seeds of crabgrass and barnyardgrass were planted in each pot having a surface area of 100 cm$^2$ and instantly an aqueous suspension prepared by diluting an emulsifiable concentrate with water to a specified concentration (2000, 1000 ppm) was sprayed on the soil surface at a rate of 100 1/10 are. The pots were kept in a greenhouse. Three weeks after treatment, the degree of damage to the each plant was observed and evaluated on the same scale as in Test 1.

The results are shown in Table 3.

TABLE 3

| Compound No. | Application Rate of Active Ingredient (g/10a) | Degree of Damage | |
|---|---|---|---|
| | | Crabgrass | Barnyardgrass |
| 1 | 200 | 10 | 10 |
| | 100 | 9 | 9 |
| 2 | 200 | 10 | 10 |
| | 100 | 10 | 10 |
| Comparative Compound 1 | 200 | 6 | 6 |
| | 100 | 3 | 3 |
| Comparative Compound 2 | 200 | 6 | 6 |
| | 100 | 3 | 4 |

Comparative compounds are the same as in Test 1.

What we claim is:

1. A cyclohexane derivative having the formula

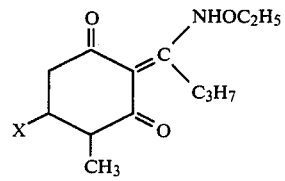

wherein X is 2-(ethylthio)propyl or 2-(4-chlorophenylthio)ethyl.

* * * * *